United States Patent [19]

Pretzer et al.

[11] 4,346,020

[45] Aug. 24, 1982

[54] NOVEL CATALYST SYSTEM AND PROCESS FOR PRODUCING ETHANOL USING SAID NOVEL CATALYST SYSTEM

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[21] Appl. No.: 220,427

[22] Filed: Dec. 29, 1980

Related U.S. Application Data

[63] Continuation-in-part of Ser. No. 42,563, May 25, 1979, abandoned, which is a continuation-in-part of Ser. No. 939,258, Sep. 5, 1978, abandoned.

[51] Int. Cl.$^3$ ............... B01J 31/28; B01J 31/04; B01J 31/02
[52] U.S. Cl. ................. 252/429 R; 252/428; 252/430; 252/431 R; 252/431 C; 252/431 P; 568/902
[58] Field of Search ............ 252/428, 429 R, 430, 252/431 R, 431 C, 431 P

[56] References Cited

U.S. PATENT DOCUMENTS

| | | | |
|---|---|---|---|
| 3,248,432 | 4/1966 | Riley et al. | 568/902 |
| 3,285,948 | 11/1966 | Rutter | 568/902 |
| 3,631,111 | 12/1971 | Tucci | 568/909 |
| 4,133,966 | 1/1979 | Pretzer et al. | 568/902 |
| 4,218,340 | 8/1980 | Holmes | 252/431 P X |
| 4,253,987 | 3/1981 | Fiato | 252/431 P X |

OTHER PUBLICATIONS

Wender et al., "Science", vol. 113, (1951), pp. 206-207.

*Primary Examiner*—Patrick Garvin
*Attorney, Agent, or Firm*—Deane E. Keith; Forrest D. Stine; Joseph J. Carducci

[57] ABSTRACT

A novel catalyst system comprising (1) a cobalt carbonyl, a hydrido cobalt carbonyl or a cobalt-containing material convertible to a cobalt carbonyl or a hydrido cobalt carbonyl, (2) a tertiary organo Group VA compound of the Periodic Table, (3) an iodine compound and (4) a ruthenium compound and to a process for selectively producing ethanol which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) a tertiary organo Group VA compound of the Periodic Table, (6) an iodine compound and (7) a ruthenium compound and then subjecting the contents of said reaction zone to an elevated temperature and an elevated pressure for a time sufficient to convert methanol to ethanol.

21 Claims, No Drawings

NOVEL CATALYST SYSTEM AND PROCESS FOR PRODUCING ETHANOL USING SAID NOVEL CATALYST SYSTEM

This application is a continuation-in-part application of our U.S. patent application Ser. No. 42,563, filed May 25, 1979 for PROCESS FOR PRODUCING ETHANOL, now abandoned, which, in turn, was a continuation-in-part application of our U.S. patent application Ser. No. 939,258, filed Sept. 5, 1978 for CRITICAL I/Co RATIOS IN A METHANOL CARBONYLATION PROCESS FOR THE SELECTIVE PRODUCTION OF ETHANOL, now abandoned.

BACKGROUND OF THE INVENTION

1. Field of the Invention

This invention is directed to a novel catalyst system comprising (1) a cobalt carbonyl, a hydrido cobalt carbonyl or a cobalt-containing material convertible to a cobalt carbonyl or a hydrido cobalt carbonyl, (2) a tertiary organo Group VA compound of the Periodic Table, (3) an iodine compound and (4) a ruthenium compound and to a process for selectively producing ethanol which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) a tertiary organo Group VA compound of the Periodic Table, (6) an iodine compound and (7) a ruthenium compound and then subjecting the contents of said reaction zone to an elevated temperature and an elevated pressure for a time sufficient to convert methanol to ethanol.

2. Description of the Prior Art

Ethanol is a compound which has been used by man since time immemorial. Historically, ethanol has been produced for various purposes by the fermentation of common grains. However, within recent years synthetic processes have been developed to synthesize this alcohol for industrial use. Such synthetic processes permit the use of more economical starting materials than those used in the fermentation processes, and additionally, permit production and reproduction of a more standardized product and more easily predictable yields of end product. Methanol can easily and economically be produced in great quantities from hydrogen and carbon monoxide or from almost anything containing carbon and hydrogen, for example, from methane to manure and from coal to crude oil residues. One such process for producing ethanol synthetically involves reacting methanol with carbon monoxide and hydrogen at elevated temperatures and pressures in the presence of a catalyst system.

The conversion of an alcohol, for example, methanol, to the primary alcohol containing one carbon atom more than the original alcohol, namely ethanol, is normally a tedious and time-consuming procedure involving a series of steps. Additionally, catalysts which possess acceptable activity generally tend to give a wide spectrum of products, in addition to ethanol, for example, hydrocarbons and oxygenated hydrocarbons having a broad distribution of carbon atoms. This not only complicates the separation and recovery of desired products, but results in reduced yield of ethanol and erosion of reactants in the production of undesirable by-products.

The reaction of methanol with hydrogen and carbon monoxide to produce ethanol is appreciated and disclosed by the prior art. However, in general, most known processes produce an undesirable large mixture of alcohols, aldehydes, ketones and carboxylic acids in addition to the desired alcohol.

For example, U.S. Pat. No. 3,285,948, entitled HALIDES OF RUTHENIUM AND OSMIUM IN CONJUNCTION WITH COBALT AND IODINE IN THE PRODUCTION OF ETHANOL FROM METHANOL, issued to Butter on Nov. 15, 1966, teaches a method for producing alcohols in which any source of cobalt soluble in the reaction medium which will yield a cobalt carbonyl or hydrogen cobalt carbonyl under the reaction conditions can be used. In addition, an iodine promoter is employed, for example, $I_2$, or alkali metal iodides. A secondary promoter is also employed, i.e., ruthenium halide or osmium halide. High selectivity is described as better when the secondary promoter is used in combination with the primary promoter and other reactants.

U.S. Pat. No. 4,013,700, entitled CATALYTIC PROCESS FOR POLYHYDRIC ALCOHOLS AND DERIVATIVES, issued to Cawse on Mar. 22, 1977, discloses a process for the preparation of polyhydric alcohols, their ether and ester derivatives, and oligomers of such alcohols. In particular, these alcohols and their derivatives are produced by reacting the oxides of carbon and hydrogen in the presence of a quaternary phosphonium cation and a rhodium carbonyl complex at elevated temperature and pressure.

Another process is set forth in U.S. Pat. No. 3,248,432, entitled PROCESS FOR THE PRODUCTION OF ETHYL ALCOHOL, issued to Riley et al on Apr. 26, 1966, which relates to a process for the production of ethyl alcohol by the interaction of methanol, carbon monoxide and hydrogen at elevated temperature and pressure in the presence of a cobalt catalyst, an iodine promoter and a phosphorus compound soluble in methanol. Examples of suitable cobalt sources are described as any water-soluble source of cobalt, for example, the cobalt carbonyls, the lower salts of alkanoate cobalt, such as cobalt acetate, cobalt formate, cobalt propionate, and the like.

U.S. Pat. No. 2,623,906, entitled PREPARATION OF ORGANIC HYDROXY-CONTAINING COMPOUNDS BY REACTING ALCOHOLS WITH CARBON MONOXIDE AND HYDROGEN, issued to Gresham on June 16, 1948, relates to a procedure for synthesizing mono and poly functional oxygen-containing organic compounds by the reaction of alcohols, carbon monoxide and hydrogen. Catalysts described as suitable for use include various cobalt compounds, for example, cobalt carbonyl, cobalt carbonyl hydride, metallic cobalt, and organic and inorganic cobalt salts. The process, however, suffers from the disadvantage of poor product distribution.

Dutch Patent No. 760.6138, entitled PROCESS FOR THE FORMATION OF ETHANOL FROM METHANOL AND SYNTHESIS GAS, issued to Shell International Research on June 8, 1976, relates to a process for producing alcohols which utilizes any soluble cobalt source which can generate a cobalt carbonyl or hydro carbonyl by reaction with the synthesis gas. For example, sources of cobalt suitable for use are cobalt iodide or cobalt metal from which ions can be generated in situ. Organic salts of cobalt such as cobalt acetate, formate, or propionate are described as especially good sources, an iodide or bromide promoter is also utilized. In addition, the use of a tertiary phosphine is described as affording improved selectivity to the formation of alcohols.

In our U.S. Pat. No. 4,133,966 dated Jan. 9, 1979, a process is disclosed for the selective formation of ethanol which comprises contacting methanol, hydrogen and carbon monoxide with a catalyst system comprising cobalt acetylacetonate, a tertiary organo Group VA compound of the Periodic Table, a first promoter comprising an iodine compound and a second promoter comprising a ruthenium compound.

SUMMARY OF THE INVENTION

The present invention relates to (1) a cobalt carbonyl, a hydrido cobalt carbonyl or a cobalt-containing material convertible to a cobalt carbonyl or a hydrido cobalt carbonyl, (2) a tertiary organo Group VA compound of the Periodic Table, (3) an iodine compound and (4) a ruthenium compound and to a process for selectively producing ethanol which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) a tertiary organo Group VA compound of the Periodic Table, (6) an iodine compound and (7) a ruthenium compound and then subjecting the contents of said reaction zone to an elevated temperature and an elevated pressure for a time sufficient to convert methanol to ethanol.

From the above it can be seen that for the purposes of the process defined and claimed herein seven separate and distinct entities are introduced into a reaction zone prior to subjecting them to an elevated temperature and elevated pressure sufficient to obtain ethanol. Of these the cobalt, the tertiary organo Group VA compound of the Periodic Table, iodine and ruthenium entities require further elucidation.

The cobalt entity is defined as being a cobalt carbonyl, a hydrido cobalt carbonyl or a cobalt-containing material convertible to a cobalt carbonyl or a hydrido cobalt carbonyl. By "cobalt carbonyl" we intend to define a compound containing only cobalt and carbon monoxide, such as $Co_2(CO)_8$ or $Co_4(CO)_{12}$. By "hydrido cobalt carbonyl" we intend to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch gauge (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt (II) sulfate, cobalt oxide ($Co_3O_4$), cobalt (II) tetrafluoroborate, cobalt (II) acetate, cobalt (II) oxalate, cobalt (II) carbonate, cobalt (II) propionate, cobalt (II) octoate, cobalt (II) butyrate, cobalt (II) benzoate, cobalt (II) valerate, cobalt (II) formate, cobalt (II) cyclohexanebutyrate, cobalt (II) 2-ethylhexoate, cobalt (II) gluconate, cobalt (II) lactate, cobalt (II) naphthenate, cobalt (II) oleate and cobalt (II) citrate.

The tertiary organo Group VA compound of the Periodic Table can be defined by the following formula:

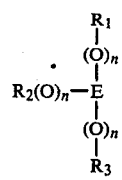

wherein E is a member selected from the group consisting of trivalent phosphorus, trivalent arsenic and trivalent antimony; and $R_1$, $R_2$ and $R_3$ are either alike or different members selected from the group consisting of saturated or unsaturated, straight or branched chain alkyl radicals having from one to 24 carbon atoms, preferably from one to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from three to 40 carbon atoms, preferably from three to 30 carbon atoms; aralkyl and alkaryl radicals having from six to 40 carbon atoms, preferably from six to 30 carbon atoms; and n is an integer of 0 or 1 with the provision that when n is 1, E must be phosphorus.

Tertiary organo Group VA compounds of the Periodic Table which are suitable for use herein include:
tri-methyl-phosphite
tri-ethyl-phosphine
tri-n-butyl-phosphine
tri-isopropyl-phosphine
tri-cyclo-hexyl-phosphite
tri-cyclo-hexyl-phosphine
tri-cyclo-heptyl-phosphine
di-phenyl-methyl-phosphine
tri-phenyl-phosphine
tri-naphthyl-phosphine
tri-styryl-phosphine
vinyl-diphenyl-phosphine
tri-benzyl-phosphite
tri-benzyl-phosphine
tri-para-tolyl-phosphite
tri-para-tolyl-phosphine
tri-ethyl-arsine
tri-n-butyl-arsine
tri-isopropyl-arsine
tri-cyclo-hexyl-arsine
tri-cyclo-heptyl-arsine
di-phenyl-methyl-arsine
tri-phenyl-arsine
tri-naphthyl-arsine
tri-styryl-arsine
vinyl-diphenyl-arsine
tri-benzyl-arsine
tri-para-tolyl-arsine
tri-ethyl-antimony
tri-n-butyl-antimony
tri-isopropyl-antimony
tri-cyclo-hexyl-antimony
tri-cyclo-heptyl-antimony
di-phenyl-methyl-antimony
tri-phenyl-antimony
tri-naphthyl-antimony
tri-styryl-antimony
vinyl-diphenyl-antimony tri-benzyl-antimony, and
tri-para-tolyl-antimony, or mixtures thereof.

Any source of iodine which is capable of disassociating, that is, ionizing to form free iodide ions in the reaction medium, can be used as a primary promoter in the present invention. Illustrative examples of iodine compounds especially suitable for use herein include iodine, lithium iodide, sodium iodide, potassium iodide, rubidium iodide, cesium iodide, magnesium iodide, calcium iodide, strontium iodide, barium iodide, stannous iodide, lead (II) iodide, bismuth (III) iodide, hydrogen iodide, methyl iodide, ethyl iodide, etc.

Any ruthenium compound can be used herein and can include, for example, ruthenium acetylacetonate, ruthenium trichloride, ruthenium tribromide, ruthenium dioxide, ruthenium triiodide, ruthenium acetate, ruthenium propionate, ruthenium octonate, ruthenium dioxide, ruthenium tetraoxide, ruthenium pentacarbonyl and tri-ruthenium dodecacarbonyl.

The relative amounts of hydrogen and carbon monoxide employed is critical in order to obtain increased ethanol yields. Thus, the molar ratio range of hydrogen to carbon monoxide must be in excess of about 1:1, preferably in excess of about 1.3:1, but most preferably in excess of about 1.5:1, but generally need not be in excess of about 4:1, preferably need not be in excess of about 2:1. Compounds or reaction mixtures which give rise to formation of carbon monoxide and hydrogen under the reaction conditions defined herein can be used instead of mixtures comprising hydrogen and carbon monoxide and hydrogen under the reaction conditions defined herein can be used instead of mixtures comprising hydrogen and carbon monoxide, which are used in the preferred embodiments of this invention.

The cobalt, iodine and ruthenium entities are introduced into the reaction zone in molar ratios, based on the elements cobalt, iodine and ruthenium, respectively, ranging from about 100:1:1 to about 1:10:2, preferably from about 20:1:1 to about 1:5:1. The cobalt entity and the Group VA compound, based on their elemental forms, can be present in a molar ratio of about 20:1 to about 1:10, preferably about 10:1 to about 1:5. Based on the methanol introduced into the system, the weight percent of combined cobalt, tertiary organo Group VA compound, iodine and ruthenium entities, in their elemental form, can range from about 0.005 to about 25 percent, preferably from about 0.01 to about 10 percent.

The process defined herein can be carried out either in a batch operation or by passing the reactants continuously through a reaction zone. In each case the reactor is provided with agitation means and the pressure is maintained therein by the addition of hydrogen and carbon monoxide as required. In order to facilitate introduction of the cobalt, tertiary Group VA compound, iodine and ruthenium entities into the reaction zone and/or to facilitate recovery of the components of the reaction herein, they can first be dissolved in an inert solvent, such as ethylene glycol, diethylene glycol monomethyl ether, acetone, sulfolanes, such as tetramethylene sulfone, lactones such as γ-butyrlactone and ε caprolactone, etc.

In the reaction zone the contents thereof are then maintained at an elevated temperature and an elevated pressure for a time sufficient to convert methanol to ethanol. Pressures which are suitable for use herein generally are above about 1000 pounds per square inch gauge (6.83 MPa), but should not be in excess of about 10,000 pounds per square inch gauge (68.30 MPa). An especially desirable pressure range is from about 1000 pounds per square inch gauge (6.83 MPa) to about 6000 pounds per square inch gauge (40.98 MPa), preferably from about 2000 pounds per square inch gauge (13.66 MPa) to about 5000 pounds per square inch gauge (34.15 MPa). Temperatures which are suitable for use herein are those temperatures which initiate a reaction between the reactants herein to produce ethanol, generally from about 150° C. to about 250° C., preferably from about 175° C. to about 225° C. The reaction is conducted for a time period sufficient to convert methanol to ethanol, normally from about 0.5 hour to about 10 hours, especially from about one to about five hours.

Recovery of the desired ethanol from the reaction product can be effected in any convenient or conventional manner, for example, by distillation. At ambient pressure and about 21° C., the components will distill off in the following sequence for the desired recovery: dimethyl ether, diethyl ether, methyl acetate, methanol and ethanol.

It is to be noted that the catalyst system herein is highly selective to the formation of ethanol and minimizes the formation of undesirable by-products such as acetaldehyde, ethers, esters and other alcohol derivatives. However, even though the by-products be termed "undesirable", they are still valuable chemicals and can be recovered and used in chemical operations.

DESCRIPTION OF PREFERRED EMBODIMENTS

The following Examples and Table serve to further illustrate and instruct one skilled in the art the best mode of how to practice this invention and to demonstrate the critical features thereof.

The reactions herein were performed in a stainless steel pressure-resistant autoclave equipped with agitation means, that is, a type 316 stainless steel, 300 cc. autoclave marketed by Autoclave Engineers. The methanol, hydrogen, carbon monoxide, the tertiary organo Group VA compound and the cobalt, iodine and ruthenium entities were introduced into the autoclave. The autoclave was connected to another larger reservoir containing synthesis gas (hydrogen and carbon monoxide) which fed said synthesis gas into the steel autoclave at a set pressure on demand. Thus the reactor pressure was maintained throughout the course of the reaction. The reaction pressure and temperature were adjusted to operating conditions and the mixture reacted for a period of time sufficient to produce ethanol.

In Example No. I there was introduced into the 300 cc. stainless steel autoclave three millimoles of cobalt-(II) acetate, 1.5 millimoles of iodine, 0.5 millimole of tri-para-tolyl-phosphite, 0.75 millimole of ruthenium(II) acetylacetonate and 100 milliliters of methanol. In Examples Nos. II to V there was introduced into the autoclave six millimoles of the cobalt entity, that is, cobalt oxide [$Co_3O_4$], cobalt(II) acetate, cobalt(II) sulfate heptahydrate [$CoSo_4.7H_2O$] and cobalt(II) tetrafluoroborate hexahydrate [$Co(BF_4)_2.6H_2O$], respectively; 1.5 millimoles of iodide; six millimoles of a tertiary organo Group VA compound, that is, triphenyl phosphine, triphenyl arsine, tri-n-butyl phosphine and triphenyl phosphine, respectively; one millimole of the ruthenium entity, that is, tri-ruthenium dodecacarbonyl, ruthenium(III) acetylacetonate, tri-ruthenium dodecacarbonyl and ruthenium(III) acetylacetonate, respectively; and 100 milliliters of methanol. The reactor was next purged twice with nitrogen gas and then pressurized with synthesis gas ($H_2$:CO molar = 1) to a pressure of about 1000 pounds per square inch (6.83 MPa) lower than the desired working pressure. The system was then heated to a temperature of about 175° C. in Example I and 200° C., in each of Examples II to V and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas test meter and a gas sample was taken for a mass spectral analysis, and the liquid product was analyzed using a Model 900 Perkin-Elmer gas chromatograph utilizing a 16 ft. (4.88 meters)×1.8 in. (0.32 centimeter) stainless steel column wherein 8 ft. (2.44 meters) of the column was packed with 80/100 mesh Poropak Q and the other 8 ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min. and with a helium flow rate of 30 cc./min. The data obtained are set forth below in Table I.

In each of Examples Nos. VI, VIII, X and XII there was introduced into the 300 cc. stainless steel autoclave 2.25 millimoles of $Co_2(CO)_8$ (0.77 gram), 4.5 millimoles of iodine, (1.14 gram), 0.45 millimole of ruthenium (III) acetylacetonate (0.18 gram) and 100 milliliters of methanol. In each of Examples Nos. VII, IX, XI and XIII there was introduced into the autoclave 2.25 millimoles of $Co(CO)_8$ (0.77 gram), 4.5 millimoles of iodine (1.14 gram), 4.5 millimoles of triphenyl phosphine (1.18 grams), 0.45 millimole of ruthenium (III) acetylacetonate (0.18 gram) and 100 milliliters of methanol. The reactor was next purged twice with nitrogen gas and then pressurized with the desired blend of hydrogen and carbon monoxide to a pressure of about 1000 pounds per square inch (6.83 MPa) lower than the desired working pressure. The system was then heated to a temperature of about 215° C. and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry test gas meter and a gas sample was taken for a mass spectral analysis, and the liquid product was analyzed using a Model 900 Perkin-Elmer gas chromatograph utilizing a 16 ft. (4.88 meters)×1.8 in. (0.32 centimeter) stainless steel column wherein 8 ft. (2.44 meters) of the column was packed with 80/100 mesh Poropak Q and the other 8 ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min. and with a helium flow rate of 30 cc./min. The data obtained are also set forth below in Table I.

In Example XIV there was introduced into the 300 cc. stainless steel autoclave 2.5 millimols of $Co_2(CO)_8$, five millimoles of triphenyl phosphine and five millimoles of iodine. The autoclave was purged twice with nitrogen gas and then pressurized with synthesis gas ($H_2$:CO molar = 1) to a pressure of 1000 pounds per square inch lower than the desired working pressure. The system was then heated to a temperature of about 200° C. and the pressure was adjusted to a working pressure of 4000 pounds per square inch. The reaction was allowed to proceed for approximately three hours, after which the reactor was cooled by an internal cooling coil to about −75° C. The reactor was vented through a dry gas meter and a gas sample was taken for a mass spectral analysis, and the liquid product was analyzed using a Model 900 Perkin-Elmer gas chromatograph utilizing a 16 ft. (4.88 meters)×1.8 in. (0.32 centimeter) stainless steel column wherein 8 ft. (2.44 meters) of the column was packed with 80/100 mesh Poropak Q and the other 8 ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min. and with a helium flow rate of 30 cc./min. The data obtained are also set forth below in Table I.

TABLE I

| Example No. | Gram Atom of P to CO | Mol Ratio of $H_2$ to CO | Percent MeOH[a] Conversion | Mole Percent Selectivity | | | | | | | | Percent Yield to Ethanol |
|---|---|---|---|---|---|---|---|---|---|---|---|---|
| | | | | $Me_2O$[b] | AcH[c] | $Et_2O$[d] | EtOH[e] | MeOAc[f] | EtOAc[g] | HOAc[h] | Other[i] | |
| I | 1:6 | 1 | 46.3 | 6.9 | 0 | 13.8 | 49.5 | 23.8 | j | j | 6.0 | 22.9 |
| II | 1:1 | 1 | 45.1 | 3.3 | 0 | 12.8 | 70.3 | 11.8 | j | j | 1.8 | 31.7 |
| III | 1:1 | 1 | 35.3 | 5.2 | 0 | 2.0 | 66.4 | 22.1 | j | j | 4.3 | 23.4 |
| IV | 1:1 | 1 | 28.1 | 6.5 | 0 | 0.8 | 76.8 | 13.0 | j | j | 2.9 | 21.6 |
| V | 1:1 | 1 | 61.5 | 21.6 | 8.8 | 7.2 | 43.0 | 16.1 | j | j | 3.3 | 26.4 |
| VI | 0 | 0.33 | 83.0 | 28.7 | 6.4 | 0 | 28.6 | 26.2 | 7.9 | 1.0 | 1.2 | 23.7 |
| VII | 1:1 | 0.33 | 84.0 | 10.5 | 10.0 | 0 | 4.9 | 58.4 | 5.4 | 1.1 | 9.7 | 4.1 |
| VIII | 0 | 1 | 93.0 | 11.3 | 4.0 | 6.0 | 50.1 | 7.45 | 15.9 | 1.87 | 3.3 | 46.6 |
| IX | 1:1 | 1 | 94.0 | 2.9 | 12.7 | 3.8 | 39.9 | 7.4 | 17.3 | 1.2 | 14.8 | 37.5 |
| X | 0 | 2 | 93.0 | 39.4 | 0.1 | 2.6 | 43.6 | 4.7 | 1.9 | 0 | 7.7 | 40.5 |
| XI | 1:1 | 2 | 77.0 | 14.0 | 1.0 | 4.2 | 72.5 | 4.5 | 1.2 | 0.6 | 2.0 | 55.8 |
| XII | 0 | 3 | 83.0 | 94.8 | 0.3 | 0 | 2.5 | 0.9 | 0 | 0 | 1.5 | 2.1 |
| XIII | 1:1 | 3 | 91.0 | 20.8 | 0.8 | 5.7 | 61.4 | 5.4 | 2.3 | 0.9 | 2.7 | 55.9 |

TABLE I-continued

| Example No. | Gram Atom of P to CO | Mol Ratio of H₂ to CO | Percent MeOH[a] Conversion | Mole Percent Selectivity | | | | | | | | Percent Yield to Ethanol |
|---|---|---|---|---|---|---|---|---|---|---|---|---|
| | | | | Me₂O[b] | AcH[c] | Et₂O[d] | EtOH[e] | MeOAc[f] | EtOAc[g] | HOAc[h] | Other[i] | |
| XIV | 1:1 | 1 | 73.0 | 13.4 | 20.8 | 2.0 | 24.0 | 19.8 | 9.5 | j | 10.5 | 17.5 |

[a]Methanol
[b]Dimethyl Ether
[c]Acetaldehyde
[d]Diethyl ether
[e]Ethanol
[f]Methyl Acetate
[g]Ethyl Acetate
[h]Acetic acid
[i]Mixtures of methane, ethane, methyl formate, propanol, n-propanol, n-butanol and n-butanal
[j]Not taken The data in Table I emphasizes the uniqueness of the presence of the novel catalyst herein and the critical necessity of maintaining molar ratios of hydrogen to carbon monoxide in excess of about 1:1 in order to obtain exceptionally high ethanol yields. Thus, from Examples Nos. I to V, inclusive, and Example No. IX it can be seen that when the novel catalyst herein is used in a homologation process wherein equal molar ratios of hydrogen and carbon monoxide are used the percent yield of ethanol obtained ranges from 21.6 to 37.5 percent. In Example No. VII when the process is repeated but the hydrogen to molar ratio is reduced to 0.33:1, the percent yield to ethanol is greatly reduced to 4.1. However, when the process is again repeated and the molar ratio of hydrogen to carbon monoxide is increased to 2:1 in Example No. XI and to 3:1 in Example No. XIII, the percent yield to ethanol is unexpectedly greatly increased to 55.8 and 55.9 percent, respectively. At molar ratios of hydrogen to carbon monoxide of 0.33:1 in Run No. VI and 1:1 in Run No. VIII, wherein the process was otherwise similar to those of Examples Nos. VII and IX, respectively, but the catalyst did not contain phosphorus, the percent yields to ethanol were higher. It was highly surprising, therefore, that when in Examples Nos. XI and XIII the process was repeated using the novel catalyst herein and with hydrogen to carbon monoxide molar ratios in excess of about 1:1, greatly increased yields to ethanol were obtained compared to Examples Nos. X and XII wherein the process was similar except that the catalyst used did not contain phosphorus. That the presence of phosphorus in a homologation catalyst would have resulted in increased yields of the magnitudes obtained in Examples Nos. XI and XII would not have been predicted is apparent from Example No. XIV wherein phosphorus was present but not ruthenium. Thus, it is clear from the data that the homologation catalyst must contain the cobalt compound, the tertiary organo Group VA compound, the iodine and the ruthenium compound.

Obviously, many modifications and variations of the invention, as hereinabove set forth, can be made without deparing from the spirit and scope thereof and, therefore, only such limitations should be imposed as are indicated in the appended claims.

We claim:

1. A novel catalyst system comprising (1) a cobalt entity selected from the group consisting of a cobalt carbonyl, a hydrido cobalt carbonyl and a cobalt-containing material convertible to a cobalt carbonyl or a hydrido cobalt carbonyl, (2) a tertiary organo Group VA compound of the Periodic Table of the formula:

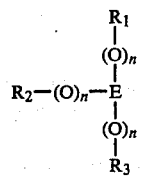

wherein E is a member selected from the group consisting of trivalent phosphorus, trivalent arsenic and trivalent antimony; and $R_1$, $R_2$, and $R_3$ are either alike or different members selected from the group consisting of saturated or unsaturated, straight or branched chain alkyl radicals having from one to 24 carbon atoms, aryl radicals having from six to 20 carbon atoms; alkenyl radicals having from two to 30 carbon atoms; cycloalkyl radicals having from three to 40 carbon atoms; aralkyl and alkaryl radicals having from six to 40 carbon atoms; and n is an integer of 0 or 1 with the provision that when n is 1, E must be phosphorus, (3) an iodine compound and (4) a ruthenium compound.

2. The catalyst system of claim 1, wherein $R_1$, $R_2$ and $R_3$ are either alike or different members selected from the group consisting of alkyl radicals having from one to 10 carbon atoms; aryl radicals having from six to 10 carbon atoms; alkenyl radicals having from two to 20 carbon atoms; cycloalkyl radicals having from about three to 30 carbon atoms; and aralkyl and alkaryl radicals having from six to about 30 carbon atoms.

3. The catalyst system of claim 1 wherein the tertiary organo Group VA compound is a member selected from the group consisting of:
tri-methyl-phosphite
tri-ethyl-phosphine
tri-n-butyl-phosphine
tri-isopropyl-phosphine
tri-cyclo-hexyl-phosphite
tri-cyclo-hexyl-phosphine
tri-cyclo-heptyl-phosphine
di-phenyl-methyl-phosphine
tri-phenyl-phosphine
tri-naphthyl-phosphine
tri-styryl-phosphine
vinyl-diphenyl-phosphine
tri-benzyl-phosphite
tri-benzyl-phosphine
tri-para-tolyl-phosphite
tri-para-tolyl-phosphine
tri-ethyl-arsine
tri-n-butyl-arsine
tri-isopropyl-arsine tri-cyclo-hexyl-arsine
tri-cyclo-heptyl-arsine
di-phenyl-methyl-arsine
tri-phenyl-arsine
tri-naphthyl-arsine
tri-styryl-arsine
vinyl-diphenyl-arsine
tri-benzyl arsine
tri-para-tolyl-arsine
tri-ethyl-antimony
tri-n-butyl-antimony tri-isopropyl-antimony
tri-cyclo-hexyl-antimony
tri-cyclo-heptyl-antimony
di-phenyl-methyl-antimony
tri-phenyl-antimony
tri-naphthyl-antimony
tri-styryl-antimony
vinyl-diphenyl-antimony
tri-benzyl-antimony, and
tri-para-tolyl-antimony, or mixtures thereof.

4. The catalyst system of claim 1 wherein the tertiary organo Group VA compound is tri-phenyl phosphine.

5. The catalyst system of claim 1 wherein the tertiary organo Group VA compound is tri-p-tolyl phosphite.

6. The catalyst system of claim 1 wherein the tertiary organo Group VA compound is triphenyl arsine.

7. The catalyst system of claim 1 wherein the tertiary organo Group VA compound is tri-n-butyl phosphine.

8. The catalyst system of claim 1 wherein the cobalt entity is cobalt (II) acetate.

9. The catalyst system of claim 1 wherein the cobalt entity is cobalt oxide.

10. The catalyst system of claim 1 wherein the cobalt entity is cobalt (II) sulfate heptahydrate.

11. The catalyst system of claim 1 wherein the cobalt entity is cobalt (II) tetrafluoroborate hexahydrate.

12. The catalyst system of claim 1 wherein the cobalt entity is cobalt carbonyl.

13. The catalyst system of claim 1 wherein the iodine compound is a member selected from the group consisting of iodine, lithium iodide, sodium iodide, potassium iodide, rubidium iodide, cesium iodide, magnesium iodide, calcium iodide, strontium iodide, barium iodide, stannous iodide, lead(II) iodide, bismuth(III) iodide, hydrogen iodide, methyl iodide, ethyl iodide, or mixtures thereof.

14. The catalyst system of claim 1 wherein the iodine compound is iodine.

15. The catalyst system of claim 1 wherein the ruthenium compound is a member selected from the group consisting of ruthenium acetylacetonate, ruthenium trichloride, ruthenium tribromide, ruthenium triiodide, ruthenium dioxide, ruthenium acetate, ruthenium propionate, ruthenium octonate, ruthenium dioxide, ruthenium tetraoxide, ruthenium pentacarbonyl and triruthenium dodecacarbonyl, or mixtures thereof.

16. The catalyst system of claim 1 wherein the ruthenium compound is ruthenium(III) acetylacetonate.

17. The catalyst system of claim 1 wherein the ruthenium compound is tri-ruthenium dodecacarbonyl.

18. The catalyst system of claim 1 wherein the cobalt, iodine and ruthenium entities are present in a molar ratio of about 100:1:1 to about 1:10:2.

19. The catalyst system of claim 1 wherein the cobalt, iodine and ruthenium entities are present in a molar ratio of about 20:1:1 to about 1:5:1.

20. The catalyst system of claim 1 wherein the cobalt entity and the Group VA compound are present in a molar ratio of about 20:1 to about 1:10.

21. The catalyst system of claim 1 wherein the cobalt entity and the Group VA compound are present in a molar ratio of about 10:1 to about 1:5.

* * * * *